(12) United States Patent
Bellman

(10) Patent No.: US 7,758,901 B2
(45) Date of Patent: *Jul. 20, 2010

(54) COMPOSITIONS AND METHODS FOR ALLEVIATING SKIN DISORDERS

(76) Inventor: Betty Bellman, 4302 Alton Rd., Suite 705, Miami Beach, FL (US) 33140-2877

( * ) Notice: Subject to any disclaimer, the term of this patent is extended or adjusted under 35 U.S.C. 154(b) by 0 days.

This patent is subject to a terminal disclaimer.

(21) Appl. No.: 12/275,644

(22) Filed: Nov. 21, 2008

(65) Prior Publication Data

US 2009/0074892 A1     Mar. 19, 2009

Related U.S. Application Data

(63) Continuation-in-part of application No. 11/739,363, filed on Apr. 24, 2007, now Pat. No. 7,488,500.

(60) Provisional application No. 60/890,447, filed on Feb. 16, 2007.

(51) Int. Cl.
*A61K 36/889* (2006.01)
(52) U.S. Cl. .................................... 424/727
(58) Field of Classification Search ............ None
See application file for complete search history.

(56) References Cited

U.S. PATENT DOCUMENTS

| 2002/0165286 A1 | 11/2002 | Hedeman et al. |
| 2003/0092754 A1 | 5/2003 | Nishimuta et al. |
| 2005/0043398 A1 | 2/2005 | Carola et al. |
| 2005/0063930 A1 | 3/2005 | Carlsson et al. |
| 2005/0100524 A1 | 5/2005 | Springstead |
| 2005/0276826 A1* | 12/2005 | Culver et al. ............... 424/401 |

FOREIGN PATENT DOCUMENTS

| KR | 1020000046633 A | 7/2000 |
| KR | 1020070000599 A | 1/2007 |
| WO | 99/11237 A1 | 3/1999 |
| WO | WO9911237 A1 | 11/1999 |
| WO | 02/47642 A1 | 6/2002 |
| WO | WO0247642 A1 | 6/2002 |
| WO | 2005/067691 A2 | 7/2005 |
| WO | WO2005067691 A2 | 7/2005 |

OTHER PUBLICATIONS

Soapers Choice (www.soaperchoice.com/soapolis/coconutoil.html), pp. 1-3.
International Preliminary Report on Patentability for PCT/US2008/054242.

* cited by examiner

*Primary Examiner*—Christopher R Tate
*Assistant Examiner*—Deborah A. Davis
(74) *Attorney, Agent, or Firm*—Flaster Greenberg, P.C.; Gary D. Colby

(57) ABSTRACT

The disclosure relates to the discovery that fractionated coconut oil is effective for alleviating existing skin disorders when applied topically to the skin of a person afflicted with such a disorder. The disclosure further relates to the discovery that fractionated coconut oil can be used to prevent or inhibit onset of a skin disorder or to reduce the severity of a skin disorder when administered prophylactically to the skin of a person. A cromolyn compound, a corticosteroid, or both, can be included in the composition.

20 Claims, No Drawings

COMPOSITIONS AND METHODS FOR ALLEVIATING SKIN DISORDERS

CROSS-REFERENCE TO RELATED APPLICATIONS

This application is a continuation-in-part of U.S. non-provisional patent application Ser. No. 11/739,363 (allowed), which was filed on 24 Apr. 2007, and is entitled to priority pursuant to 35 U.S.C. §119(e) to U.S. provisional patent 60/890,447 which was filed on 16 Feb. 2007.

BACKGROUND OF THE DISCLOSURE

The disclosure relates generally to the field of skin care and alleviation of skin disorders.

Numerous skin disorders are known in the art, including atopic dermatitis, eczema, and dry skin, for example. Such disorders include those associated with dryness, loss of suppleness, itching, redness, cracking, flaking, and other common symptoms.

BRIEF SUMMARY OF THE DISCLOSURE

The invention relates to a method of alleviating a skin disorder in a person. The method comprises applying fractionated coconut oil to at least a portion of the skin affected by the disorder. The composition containing the fractionated coconut oil preferably includes no other skin-active agents, other than (optionally) one or both of a cromolyn compound and a corticosteroid.

The invention also relates to a method of inhibiting development of a skin disorder in a portion of the skin of a person. This method comprises applying fractionated coconut oil to the portion in an amount sufficient to inhibit development of the disorder. The composition containing the fractionated coconut oil preferably includes no other skin-active agents, other than (optionally) one or both of a cromolyn compound and a corticosteroid.

DETAILED DESCRIPTION

The disclosure relates to compositions and methods for alleviating skin disorders.

It has been discovered that application of fractionated coconut oil to the skin of a person afflicted with a skin disorder (including atopic dermatitis, eczema, and dry skin, for example) alleviates the disorder in the person, returns the person's skin to a more nearly normal and healthy condition, improves the appearance of the skin, and improves the person's satisfaction with his or her skin. Furthermore, application of fractionated coconut oil can prevent or inhibit the onset or severity of a skin disorder.

Coconut oil is an oil extracted from the flesh of coconuts (e.g., coconuts of the species *Cocos nucifera*). It is a fat consisting of about 90% saturated fat. The oil contains mostly medium chain triglycerides, with about 87% saturated fatty acids, 6% monounsaturated fatty acids, and 2% polyunsaturated fatty acids. Coconut oil is known to contain several different saturated fatty acids. Nonetheless, about 45% of the saturated fatty acids are lauric acid, about 17% are myristic acid, and about 8% are palmitic acid. Monounsaturated fatty acids in coconut oil include primarily oleic acid, and the only polyunsaturated fatty acid generally present is linoleic acid.

"Fractionated coconut oil" is a fraction of the whole oil, in which most of the long-chain triglycerides are removed, leaving only saturated fats in the fractionated oil. Fractionated coconut oil (FCO) is sometimes referred to as "caprylic/capric triglyceride" or MCT oil because mostly the medium-chain triglycerides (caprylic and capric acid) are left in the oil.

FCO tends to lack the scent normally associated with coconut oil (or, more properly, with the portions of coconut oil not present in FCO). FCO has a very light and clean skin feel, applies smoothly, and tends to dry more quickly than other known skin oils.

In the methods described herein, a person afflicted with a skin disorder applies FCO to their skin, or to the portions of the skin affected by the disorder. The amount of FCO is not critical, and can be about as much oil as will ordinarily adhere to the skin at room temperature. Because FCO is not believed to exhibit any significant toxicity, it can be applied to the skin liberally, generally as often as desired by the person. In general, the FCO should be applied to the skin not less frequently than about once every few days, and not more frequently than every two hours, and preferably once or twice per day. This higher frequency is not dictated by safety or operability. Nonetheless, it is recognized that, at high application frequencies, the efficacy of the composition may be little or no greater than at lower application frequencies.

Similarly, FCO can be applied to the skin of a healthy person (i.e., a person who is not afflicted with a skin disorder, or who is not recognized as being afflicted with a skin disorder) in order to prevent or delay the onset of the skin disorder, or to reduce the severity of the skin disorder should it occur.

As a general guideline, the amount of FCO applied to the skin should be an amount sufficient to create a film of the oil on the skin, and not more than the amount that will adhere to the skin without dripping. This amount is believed to be approximately 5 milliliters per square meter of skin surface, although this amount is merely an estimate. Approximately 0.5 milliliters of FCO is sufficient to apply to front half of the thigh of an adult woman, for example.

The form in which the FCO is applied is not critical. Generally, because FCO is a liquid at room temperature, it can be applied as a fluid. By way of example, the FCO can be applied using a spray device or atomizer, by pouring or rubbing it onto the skin, by daubing it onto the skin using a sponge or brush, by rolling it on using a 'ball point pen' or 'roll-on deodorant' type container, or otherwise. Although the FCO is preferably applied as a liquid, it can be incorporated into a variety of bases or vehicles, such as creams, lotions, mousses, foams, pastes, or the like. Similarly, if applied below its congealing temperature, FCO can be applied as a solid, for example by rubbing or wiping the solid FCO onto the skin.

Specific examples of skin disorders that can be alleviated or prevented by topical application of FCO to the skin include atopic dermatitis, eczema, and dry skin. This list of disorders is not limiting. Other skin disorders can be similarly treated.

Patients of the applicant who have been afflicted with skin disorders and to whose skin FCO was applied as a spray (patients were instructed to apply FCO at least once per day to affected areas and told that it could be applied more frequently if desired) reported relief from their symptoms and general satisfaction with the skin characteristics obtained upon using the product.

One or more cromolyn compounds (e.g., cromolyn sodium) can be added to the composition to enhance its effectiveness and to alleviate additional symptoms. Cromolyn compounds are known mast cell stabilizing agents that can prevent release of histamine from mast cells. When combined with FCO in a topically-applied composition, the composition can have the effects described herein for FCO and can also alleviate or prevent inflammation, itching, and irritation and decrease the severity of the same. When combined with FCO in a topically-applied composition, a cromolyn compound such as cromolyn sodium can, for example, be included in an amount of about 1% to about 10% by weight. Greater or lesser amounts can be added.

One or more corticosteroids (e.g., hydrocortisone) can be added to the composition, instead of or in addition to cromolyn compounds, in order to enhance the effectiveness of the composition and to alleviate additional symptoms. Numerous corticosteroids are known in the art (e.g., hydrocortisone, desonide, alclometasone dipropionate, and methyl prednisone), and the identity of the corticosteroid added is not critical. Corticosteroids can be added in effective amounts typically used in other topical compositions. For example, it is known to include hydrocortisone in amounts up to 1% (e.g. 0.1%-1%) in topical consumer products sold without a prescription and in amounts greater than 1% in products available in the U.S. by prescription only. The form in which the corticosteroid is added to the composition is similarly immaterial. Suitable compositions can include corticosteroid incorporated in powdered form or in an aqueous solution (e.g., the composition can be a water-in-oil, oil-in-water, or other emulsion), for example.

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. A method of alleviating a skin disorder selected from the group consisting of atopic dermatitis and eczema in a person, the method comprising applying to at least a portion of the skin affected by the disorder a composition consisting essentially of fractionated coconut oil and at least one additional ingredient selected from the group consisting of cromolyn compounds and corticosteroids.

2. The method of claim 1, wherein the additional ingredient is a cromolyn compound.

3. The method of claim 2, wherein the cromolyn compound is cromolyn sodium.

4. The method of claim 2, wherein the cromolyn compound is present in an amount from 1% to about 10% by weight of the composition.

5. The method of claim 1, wherein the additional ingredient is a corticosteroid.

6. The method of claim 5, wherein the corticosteroid is hydrocortisone.

7. The method of claim 5, wherein the corticosteroid is present in an amount from 0.1% to about 1% by weight of the composition.

8. The method of claim 1, wherein the composition consists essentially of fractionated coconut oil, a cromolyn compound, and a corticosteroid.

9. The method of claim 1, wherein the composition consists essentially of fractionated coconut oil, cromolyn sodium, and hydrocortisone.

10. The method of claim 1, wherein the composition consists essentially of fractionated coconut oil, cromolyn sodium in an amount from 1% to about 10% by weight of the composition, and hydrocortisone in an amount from 0.1% to about 1% by weight of the composition.

11. A method of inhibiting development of a skin disorder selected from the group consisting of atopic dermatitis and eczema in a portion of the skin of a person afflicted with the disorder, the method comprising applying to the portion of the skin, in an amount sufficient to inhibit development of the disorder, a composition consisting essentially of fractionated coconut oil and at least one additional ingredient selected from the group consisting of cromolyn compounds and corticosteroids.

12. The method of claim 11, wherein the additional ingredient is a cromolyn compound.

13. The method of claim 12, wherein the cromolyn compound is cromolyn sodium.

14. The method of claim 12, wherein the cromolyn compound is present in an amount from 1% to about 10% by weight of the composition.

15. The method of claim 11, wherein the additional ingredient is a corticosteroid.

16. The method of claim 15, wherein the corticosteroid is hydrocortisone.

17. The method of claim 15, wherein the corticosteroid is present in an amount from 0.1% to about 1% by weight of the composition.

18. The method of claim 11, wherein the composition consists essentially of fractionated coconut oil, a cromolyn compound, and a corticosteroid.

19. The method of claim 11, wherein the composition consists essentially of fractionated coconut oil, cromolyn sodium, and hydrocortisone.

20. The method of claim 11, wherein the composition consists essentially of fractionated coconut oil, cromolyn sodium in an amount from 1% to about 10% by weight of the composition, and hydrocortisone in an amount from 0.1% to about 1% by weight of the composition.

* * * * *